US010209504B2

(12) United States Patent
Kubo et al.

(10) Patent No.: US 10,209,504 B2
(45) Date of Patent: Feb. 19, 2019

(54) LIGHT DETECTING DEVICE AND LASER MICROSCOPE SYSTEM

(71) Applicants: OLYMPUS CORPORATION, Hachioji-shi, Tokyo (JP); NATIONAL INSTITUTE OF INFORMATION AND COMMUNICATIONS TECHNOLOGY, Koganei-shi, Tokyo (JP); OSAKA UNIVERSITY, Suita-shi, Osaka (JP); NATIONAL UNIVERSITY CORPORATION HOKKAIDO UNIVERSITY, Sapporo-shi, Hokkaido (JP)

(72) Inventors: Hirokazu Kubo, Tokyo (JP); Shigehito Miki, Hyogo (JP); Hirotaka Terai, Hyogo (JP); Taro Yamashita, Hyogo (JP); Tokuko Haraguchi, Hyogo (JP); Yasushi Hiraoka, Hyogo (JP); Masataka Kinjo, Hokkaido (JP)

(73) Assignees: OLYMPUS CORPORATION, Tokyo (JP); NATIONAL INSTITUTE OF INFORMATION AND COMMUNICATIONS TECHNOLOGY, Tokyo (JP); OSAKA UNIVERSITY, Osaka (JP); NATIONAL UNIVERSITY CORPORATION HOKKAIDO UNIVERSITY, Hokkaido (JP)

( * ) Notice: Subject to any disclaimer, the term of this patent is extended or adjusted under 35 U.S.C. 154(b) by 0 days.

(21) Appl. No.: 15/937,684

(22) Filed: Mar. 27, 2018

(65) Prior Publication Data

US 2018/0284413 A1    Oct. 4, 2018

(30) Foreign Application Priority Data

Apr. 3, 2017 (JP) .................................. 2017-073548

(51) Int. Cl.
*G02B 21/18* (2006.01)
*G02B 21/00* (2006.01)
(Continued)

(52) U.S. Cl.
CPC ......... *G02B 21/18* (2013.01); *G01N 21/6458* (2013.01); *G02B 21/008* (2013.01);
(Continued)

(58) Field of Classification Search
CPC ....... G01N 21/6458; G01N 2201/0231; G01N 2201/06113; G02B 21/0048;
(Continued)

(56) References Cited

U.S. PATENT DOCUMENTS

| 5,583,342 | A | 12/1996 | Ichie |
| 5,796,112 | A | 8/1998 | Ichie |
| 2015/0146200 | A1* | 5/2015 | Honda ................. G01N 21/956 356/237.5 |

FOREIGN PATENT DOCUMENTS

| EP | 0627643 A2 | 12/1994 |
| JP | 2931268 B2 | 8/1999 |

(Continued)

OTHER PUBLICATIONS

Johtaro Yamamoto, et al., "Rotational diffusion measurements using polarization-dependent fluorescence correlation spectroscopy based on superconducting nanowire single-photon detector," Optics Express 32633, vol. 23, No. 25, Aug. 11, 2015, 10 Pages.

*Primary Examiner* — Mark R Gaworecki
(74) *Attorney, Agent, or Firm* — Holtz, Holtz & Volek PC

(57) ABSTRACT

Provided is a light detecting device including: a light path branching unit that branches a single detection light path of fluorescence from a specimen, into a plurality of branched light paths; a plurality of light detectors that are provided to the respective branched light paths branched by the light (Continued)

path branching unit and that include an SSPD or Geiger mode APD to detect the fluorescence; and a signal adder that generates a single image signal in accordance with the detection signals outputted from the plurality of light detectors.

15 Claims, 10 Drawing Sheets

(51) Int. Cl.
    *G01N 21/64*     (2006.01)
    *G02B 21/28*     (2006.01)

(52) U.S. Cl.
    CPC ......... *G02B 21/0076* (2013.01); *G02B 21/28* (2013.01); *G01N 2201/0231* (2013.01); *G01N 2201/06113* (2013.01); *G02B 21/0048* (2013.01)

(58) Field of Classification Search
    CPC .. G02B 21/0076; G02B 21/008; G02B 21/18; G02B 21/28
    See application file for complete search history.

(56) References Cited

FOREIGN PATENT DOCUMENTS

| | | | |
|---|---|---|---|
| JP | 2013019777 A | 1/2013 | |
| JP | 2013156238 A | 8/2013 | |

\* cited by examiner

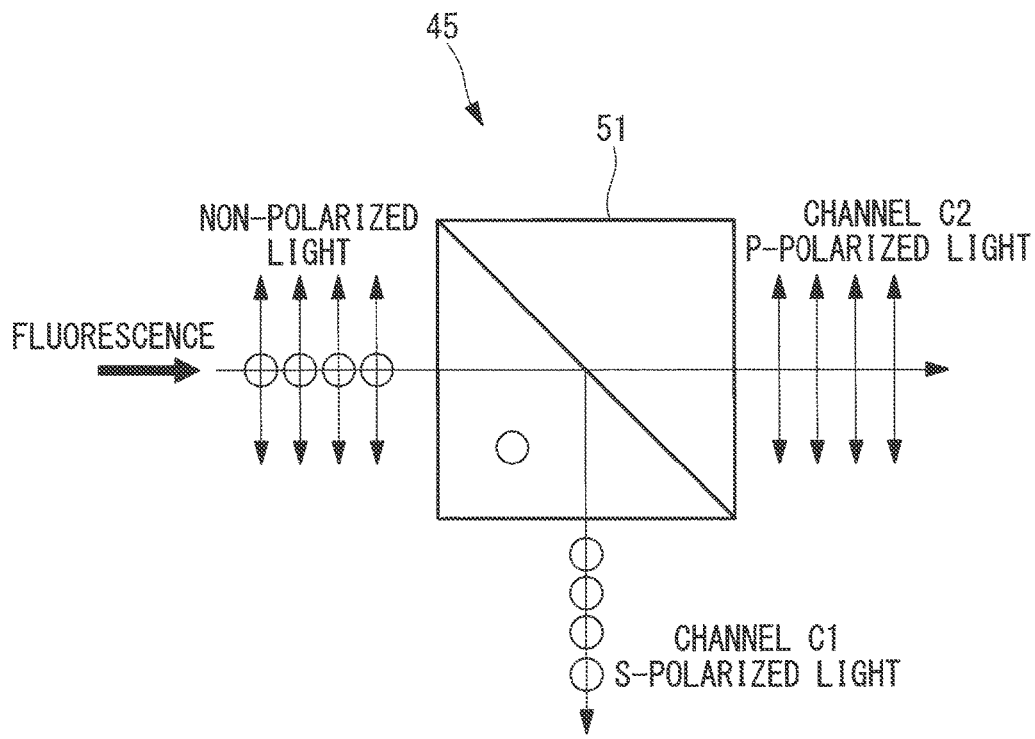
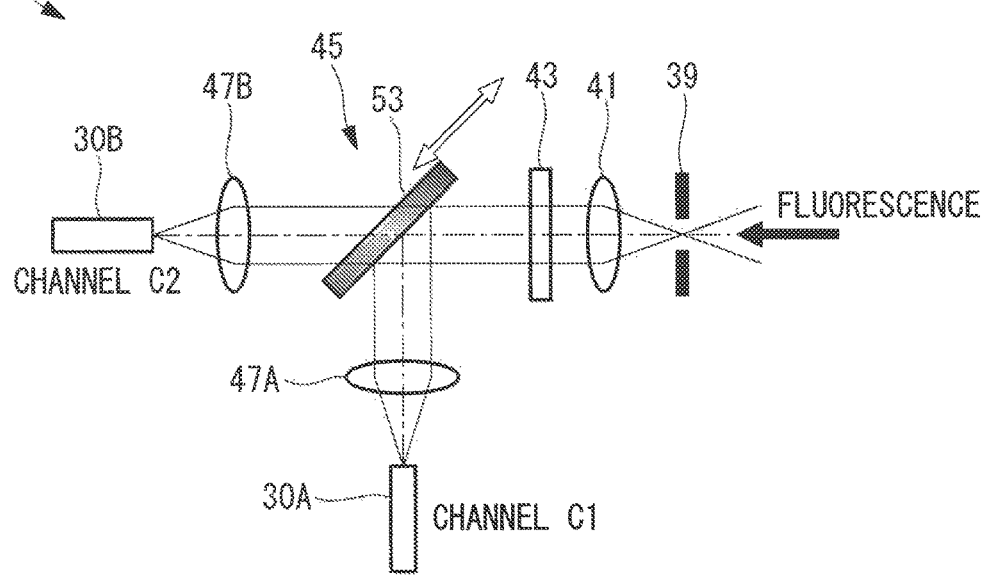

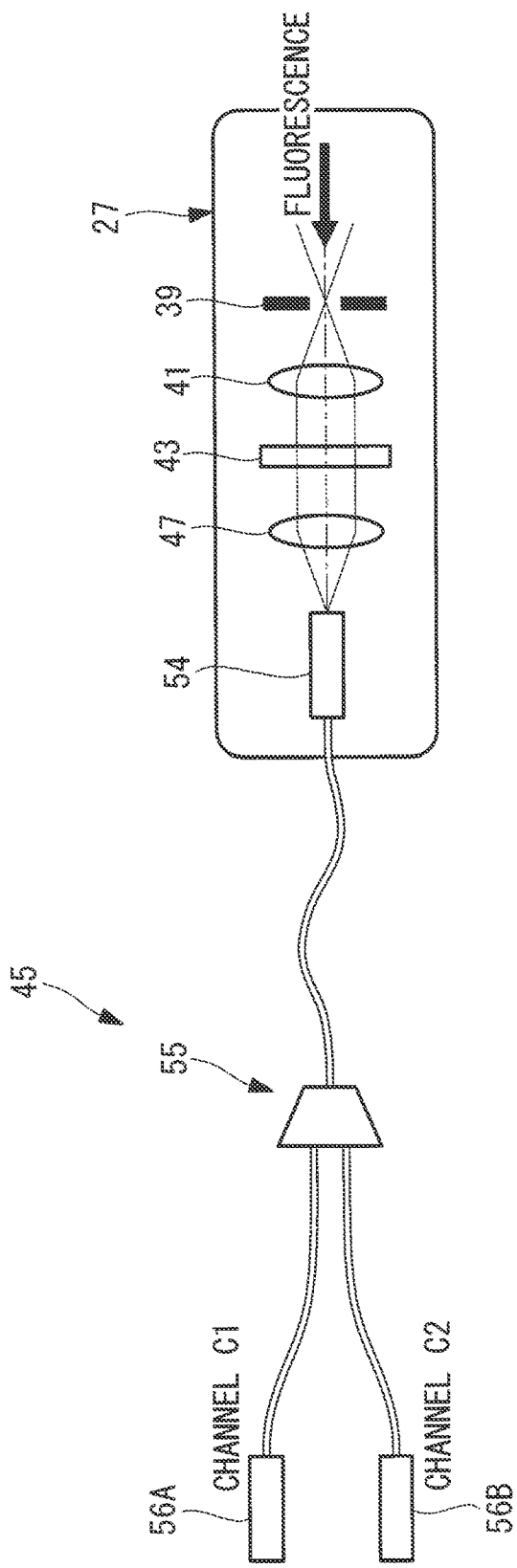

LIGHT DETECTING DEVICE AND LASER MICROSCOPE SYSTEM

CROSS-REFERENCE TO RELATED APPLICATIONS

This application is based on Japanese Patent Application No. 2017-073548, the contents of which are incorporated herein by reference.

TECHNICAL FIELD

The present invention relates to a light detecting device and a laser microscope system.

BACKGROUND ART

A laser microscope apparatus has been known in which an SSPD (superconducting nanowire single photon detector) is used as a detector in place of a PMT (photomultiplier tube) (see, for example, NPL 1). Also, a configuration including an SSPD array of four SSPDs as a light detector has been known in which a multi-pixel light receiving element is formed for one photon input so that a light receiving area per one pixel is decreased to improve the detection efficiency and the response speed (see, for example, PTL 1).

CITATION LIST

Patent Literature

{PTL 1}
Japanese Unexamined Patent Application, Publication No. 2013-019777

Non Patent Literature

{NPL 1}
Johtaro Yamamoto, Masataka Kinjo, et al., "Rotational diffusion measurements using polarization-dependent fluorescence correlation spectroscopy based on superconducting nanowire single-photon detector" 14 Dec. 2015, Vol. 23, No. 25, DOI:10.1364/OE.23.032633, OPTICS EXPRESS 32633

SUMMARY OF INVENTION

The present invention provides the following solutions.

A first aspect of the present invention is a light detecting device including: a light path branching unit that branches a single detection light path of observation light from a specimen, into a plurality of branched light paths; a plurality of light detectors that are provided to the respective branched light paths branched by the light path branching unit and include an SSPD or Geiger mode APD to detect the observation light; and a signal generating unit that generates a single image signal in accordance with detection signals outputted from the plurality of light detectors.

A second aspect of the present invention is a laser microscope system including: a light scanning unit that scans, on the specimen, laser light emitted from a laser light source; any one of the light detecting devices that detects the observation light returning from the specimen after the scanning with the laser light by the light scanning unit; and a cryocooler that cools the light detectors formed of the SSPD or the Geiger mode APD in the light detecting device.

BRIEF DESCRIPTION OF DRAWINGS

FIG. 6 is a schematic diagram illustrating one example of a light path branching unit in a laser microscope system according to a first modification of the first embodiment of the present invention.

FIG. 7 is a schematic diagram illustrating one example of a light path branching unit in a laser microscope system according to a second modification of the first embodiment of the present invention.

FIG. 8 is a schematic diagram illustrating one example of a light path branching unit in a laser microscope system according to a third modification of the first embodiment of the present invention.

DESCRIPTION OF EMBODIMENTS

First Embodiment

A light detecting device and a laser microscope system according to a first embodiment of the present invention are described below with reference to the drawings.

Figure 1:
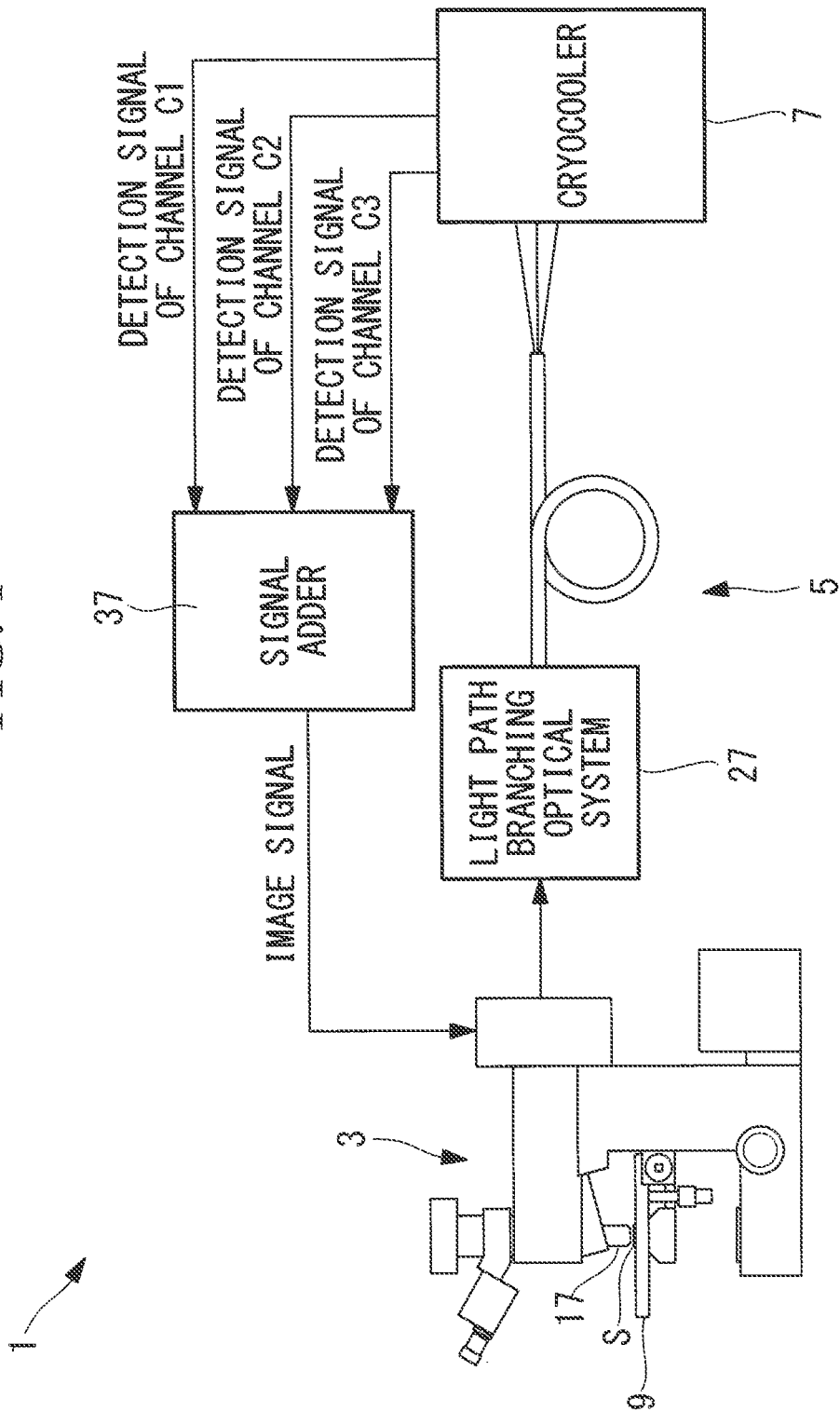
FIG. 1 is an entire configuration diagram illustrating a laser microscope system according to a first embodiment of the present invention.

As illustrated in FIG. 1, a laser microscope system 1 according to the present embodiment includes a microscope main body 3, a light detecting device 5 provided with a light path branching optical system 27 and a signal adder (signal generating unit) 37, and a cryocooler 7.

Figure 2:
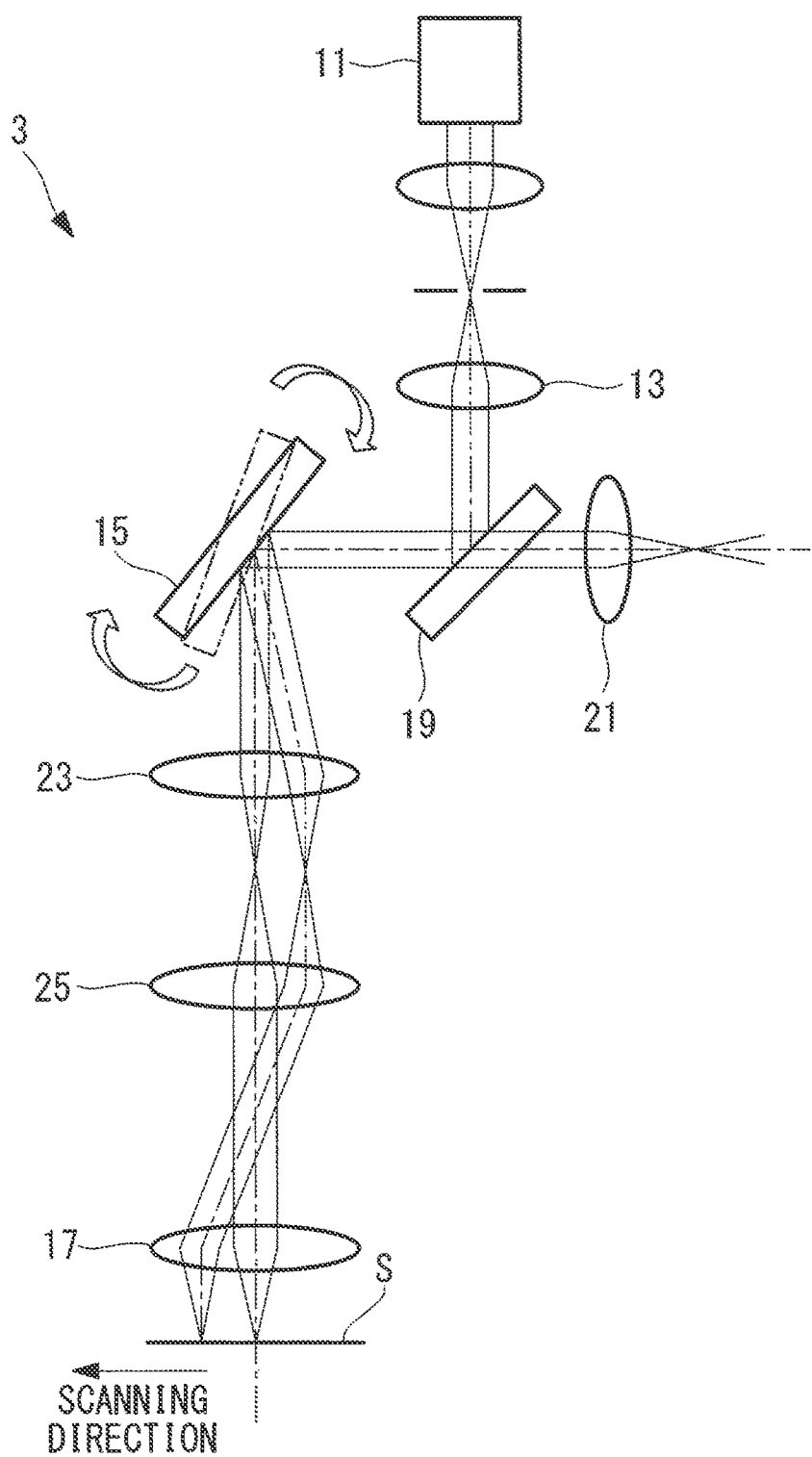
FIG. 2 is a schematic diagram illustrating the configuration of a microscope main body of the laser microscope system in FIG. 1.

As illustrated in FIGS. 1 and 2, the microscope main body 3 includes a stage 9 on which a specimen S is placed, a collimate lens 13 that converts laser light emitted from a laser light source 11 to substantially parallel light, a galvano mirror (light scanning unit) 15 that two-dimensionally scan the substantially parallel laser light converted by the collimate lens 13, an objective lens 17 that collects, on the specimen S, the laser light scanned by the galvano mirror 15 while collecting fluorescence (observation light) generated at the specimen S, a dichromic mirror 19 that causes the fluorescence returning via the galvano mirror 15 through the light path of the laser light after being collected by the objective lens 17, to branch off the light path of the laser light, and a collecting lens 21 that collects the fluorescence branched by the dichromic mirror 19. In the drawings, reference numerals 23 and 25 are a pupil projection lens and an image forming lens which relay the laser light and the fluorescence.

Figure 3:
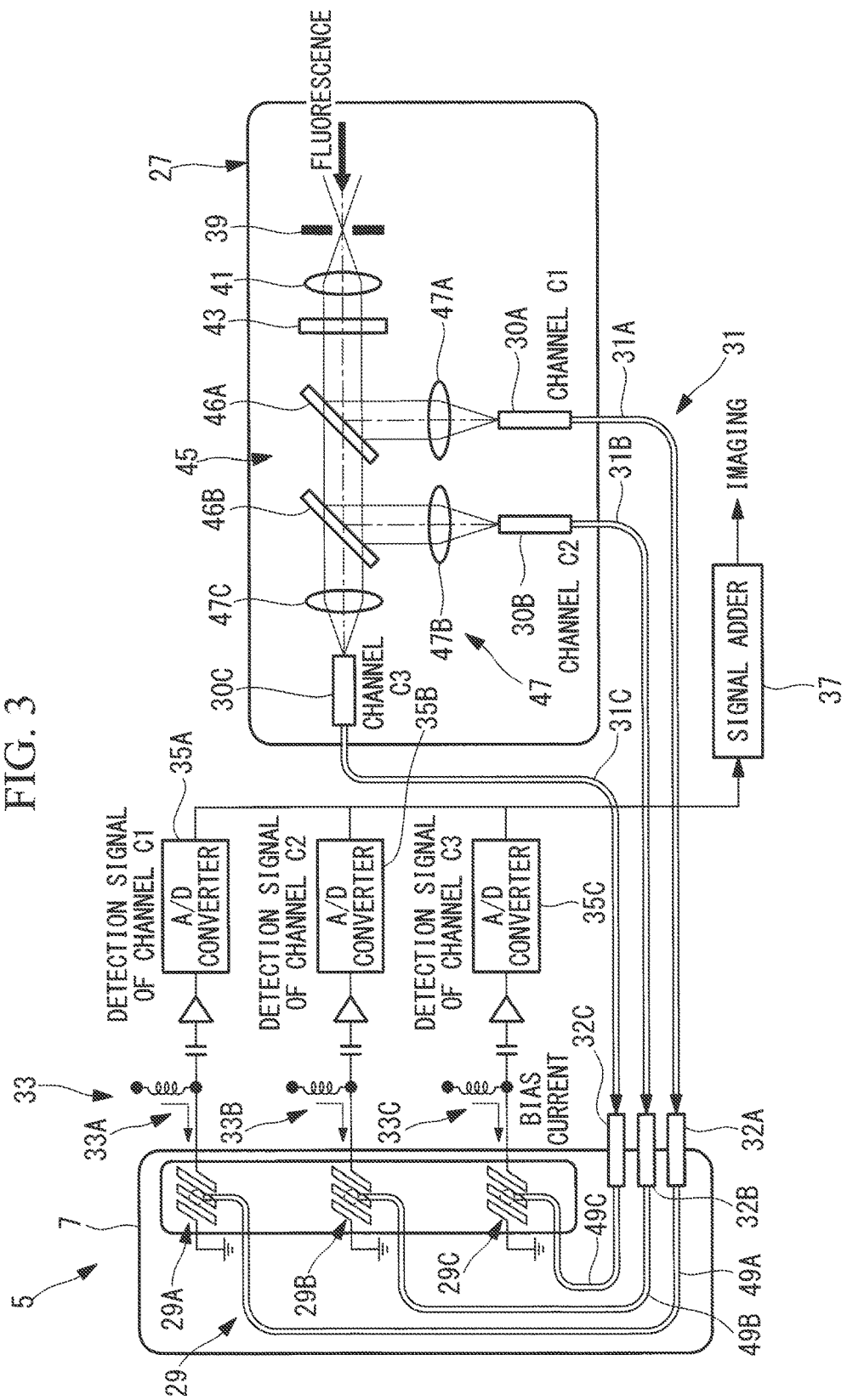
FIG. 3 is a schematic diagram illustrating a light path branching optical system and a cryocooler in the laser microscope system in FIG. 1.

As illustrated in FIGS. 1 and 3, the light detecting device 5 includes a light path branching optical system 27 connected to the microscope main body 3, a plurality of light detectors 29 (hereinafter, denoted by reference characters 29A, 29B, and 29C) that detect the fluorescence generated from the specimen S, a plurality of optical fibers 31 (hereinafter, denoted by reference characters 31A, 31B, and 31C) connecting the light path branching optical system 27 to the cryocooler 7, detection circuits 33 (hereinafter, denoted by reference characters 33A, 33B, and 33C) that output detection signals of the fluorescence detected by the light detectors 29A, 29B, and 29C, and a signal adder 37 that adds together the detection signals outputted from the detection circuits 33A, 33B, and 33C. In the drawings, reference characters 35A, 35B, and 35C denote A/D converters.

As illustrated in FIG. 3, the light path branching optical system 27 includes a confocal pinhole 39 that allows, of the fluorescence collected by the collecting lens 21 of the microscope main body 3, only fluorescence that has been generated at the focal position of the objective lens 17, to pass therethrough, a collimate lens 41 that converts the fluorescence having passed through the confocal pinhole 39 to substantially parallel light, a bandpass filter 43 that blocks laser light included in the fluorescence of the substantially parallel light converted by the collimate lens 41, a light path branching unit 45 that branches a detection light path of the fluorescence having passed through the bandpass filter 43 into a plurality of channels (branched light paths) C1, C2, and C3, and three collecting lenses 47 (hereinafter, denoted by reference characters 47A, 47B, and 47C) that collect fluorescence of the channels C1, C2, and C3, respectively, which are branched by the light path branching unit 45.

The light path branching unit 45 includes two partial reflection mirrors 46 (hereinafter, denoted by reference characters 46A and 46B) such as half mirrors.

The partial reflection mirror 46A reflects a part of the incident fluorescence according to the reflection characteristics so as to branch the part into the channel C1, while allowing the rest part of the incident fluorescence to pass through the partial reflection mirror 46A according to the transmission characteristics so as to cause the rest part to enter the partial reflection mirror 46B.

The partial reflection mirror 46B reflects a part of the incident fluorescence according to the reflection characteristics so as to branch the part into the channel C2, while allowing the rest part of the incident fluorescence to pass through the partial reflection mirror 46B according to the transmission characteristics so as to branch the rest part into the channel C3.

The optical fibers 31A, 31B, and 31C are multimode fibers that respectively guide the fluorescence in the channels C1, C2, and C3 to the cryocooler 7. The optical fibers 31A, 31B, and 31C include fiber entrance ends 30A, 30B, and 30C connected to the light path branching optical system 27, and fiber exit ends 32A, 32B, and 32C connected to the cryocooler 7, such that the fluorescence in the channels C1, C2, and C3 is caused to enter through the fiber entrance ends 30A, 30B, and 30C and exit from the fiber exit ends 32A, 32B, and 32C.

Each of the light detectors 29A, 29B, 29C is formed of an SSPD so as to output, to the outside, a voltage signal corresponding to the number of photons of light incident thereon. The light detectors 29A, 29B, 29C are provided on a sample base inside the cryocooler 7, and operate by receiving a supply of bias current from a current supply unit (not illustrated).

As illustrated in FIG. 3, the cryocooler 7 includes optical fibers 49A, 49B, and 49C connecting the three light detectors 29A, 29B, and 29C housed in the cryocooler 7 to the fiber exit ends 32A, 32B, and 32C of the optical fibers 31A, 31B, and 31C, such that the fluorescence guided through the optical fibers 31A, 31B, and 31C is guided to the light detectors 29A, 29B, and 29C through the optical fibers 49A, 49B, and 49C. Moreover, the cryocooler 7 cools the light detectors 29A, 29B, and 29C in a cryogenic state so as to hold the light detectors 29A, 29B, and 29C in a superconductive state.

Upon incidence of photons on the light detectors 29A, 29B, and 29C, the detection circuits 33A, 33B, and 33C output, as detection signals, voltage changes which are caused when a superconductive state of a superconductor is changed to a normal conductive state.

As shown in the following equation (1), the signal adder 37 generates a single image signal by adding the detection signals inputted via the A/D converters 35A, 35B, and 35C after being outputted from the detection circuits 33A, 33B, and 33C.

Image signal=detection signal of channel $C1$ from light detector $29A$+detection signal of channel $C2$ from light detector $29B$+detection signal of channel $C3$ from light detector $29C$ (1)

A single image signal generated by the signal adder 37 is transmitted, to a PC (personal computer, not illustrated), etc., to be imaged.

Next, operations of the light detecting device 5 and the laser microscope system 1 configured as described above are described.

In a case where the specimen S is observed with use of the laser microscope system 1 according to the present embodiment, the specimen S is placed on the stage 9 in the microscope main body 3 and laser light is emitted from the laser light source 11.

The laser light emitted from the laser light source 11 is converted to substantially parallel light by the collimate lens 13, is deflected by the dichromic mirror 19, and is incident on the galvano mirror 15. The laser light having been two-dimensionally scanned by an operation of the galvano mirror 15 is collected on the specimen S by the objective lens 17 after passing through the pupil projection lens 23 and the image forming lens 25.

In the specimen S, fluorescence is generated by excitation of fluorescence substances at scanning positions of the laser light. The generated fluorescence is collected by the objective lens 17, and passes through the dichromic mirror 19 on the way back via the image forming lens 25, the pupil projection lens 23, and the galvano mirror 15. Accordingly, the fluorescence is branched off the light path of the laser light, is collected by the collecting lens 21, and is incident on the light path branching optical system 27.

Of the fluorescence incident on the light path branching optical system 27, fluorescence having passed through the confocal pinhole 39 is converted to substantially parallel light by the collimate lens 41, such that light outside a fluorescent wavelength range to be observed by the bandpass filter 43 is eliminated. The fluorescence is branched, according to the wavelength characteristics, into two light paths by the partial reflection mirror 46A first, and further, one of the light paths is branched, according to the wavelength characteristics, into two light paths by the partial reflection mirror 46B next. As a result, fluorescence of a single detection light path is branched into the three channels C1, C2, and C3.

The fluorescence having been branched into the channels C1, C2, and C3 is collected by the collecting lenses 47A, 47B, and 47C, respectively, so as to enter the fiber entrance ends 30A, 30B, and 30C, and is guided through the optical fibers 31A, 31B, and 31C, so as to exit from the fiber exit ends 32A, 32B, and 32C, which are connected to the cryocooler 7.

In the cryocooler 7, the fluorescence having exited from the fiber exit ends 32A, 32B, and 32C is guided to the different light detectors 29A, 29B, and 29C by the optical fibers 49A, 49B, and 49C, respectively, and is detected by the light detectors 29A, 29B, and 29C.

When voltage changes have occurred as a result of detection of the fluorescence at the light detectors 29A, 29B, and 29C, the detection circuits 33A, 33B, and 33C generate respective detection signals in accordance with the voltage changes. The detection signals generated by the detection circuits 33A, 33B, and 33C are inputted to the signal adder 37 via the A/D converters 35A, 35B, and 35C, and are added together by the signal adder 37. As a result, the signal adder 37 generates a single image signal, and the generated image signal is transmitted, to a PC, etc. (not illustrated), to be imaged.

As described above, with the light detecting device 5 and the laser microscope system 1 according to the present embodiment, a single detection light path of fluorescence generated at the specimen S is branched into the three channels C1, C2, and C3 through the two partial reflection mirrors 46A and 46B, and the fluorescence in the channels C1, C2, and C3 is detected by the light detectors 29A, 29B, and 29C each formed of an SSPD, respectively. Accordingly, while the incident light quantity of each of the light detectors 29A, 29B, and 29C is suppressed so that saturation is avoided, the number of photons that are countable per unit time can be increased by the number of the light detectors 29A, 29B, and 29C, whereby the maximum counting rate of photons can be improved.

In this case, the signal adder 37 generates a single image signal in accordance with the detection signals obtained from the light detectors 29A, 29B, and 29C. Accordingly, the saturation level of luminance when imaging is performed can be further improved, compared to a case where one light detector is used. In addition, since the total number of the light detectors may be arbitrarily increased and reduced, the saturation level of luminance when imaging is performed can be further improved, compared to a case where one photon is detected by a multi-pixel light receiving element, as in PTL 1.

Furthermore, the fluorescence in the channels C1, C2, and C3 is detected by the light detectors 29A, 29B, and 29C, which are formed of SSPDs and which are cooled to a cryogenic temperature by the cryocooler 7 so as to be held in a superconductive state. Accordingly, the fluorescence can be detected with high quantum efficiency and low dark noise. Moreover, the light detectors 29A, 29B, and 29C are cooled by the single cryocooler 7. Accordingly, a space required for the cryocooler 7 can be greatly reduced and the cost of the cryocooler 7 can be greatly reduced, compared to a case where the light detectors 29A, 29B, and 29C are cooled by the respective cryocoolers 7. In addition, the light detectors 29A, 29B, and 29C are cooled by the single cryocooler 7. Accordingly, variation in the cooling temperature among the light detectors 29A, 29B, and 29C is eliminated so that performance stability among the light detectors 29A, 29B, and 29C can be obtained.

In the present embodiment, the light path branching optical system 27 and the cryocooler 7 are connected to each other by the optical fibers 31A, 31B, and 31C. However, the light path branching optical system 27 and the cryocooler 7 may be connected to each other by glass rods in place of the optical fibers 31A, 31B, and 31C, or fluorescence may be guided to the cryocooler 7 via an air light path with use of a mirror.

The present embodiment has the configuration in which the detection circuits 33A, 33B, and 33C, the A/D converters 35A, 35B, and 35C, and the signal adder 37 are disposed outside the cryocooler 7. Alternatively, the detection circuits 33A, 33B, and 33C, the A/D converters 35A, 35B, and 35C, and the signal adder 37 may be disposed inside the cryocooler 7.

In the present embodiment, the light detectors 29A, 29B, and 29C each of which is formed of an SSPD are provided. However, the number of the light detectors is not limited to three as long as the number is two or greater. In addition, at least one of the plurality of light detectors may be formed of an SSPD or a Geiger mode APD (avalanche photodiode).

For example, a light detector formed of an SSPD or a Geiger mode APD and a light detector formed of a PMT (a photomultiplier tube) may be combined. The Geiger mode refers to an operation mode in which a factor for multiplying photocurrent is made greatly large by setting of reverse voltage to be applied to an APD to breakdown voltage or larger, such that, when light is detected, a signal having a constant intensity is outputted, irrespective of the intensity of the light.

At least one of the light detectors may be formed by an array of a plurality of SSPDs or Geiger mode APDs. Even if the number of photons that are detectable per unit time by each of the SSPDs or Geiger mode APDs arranged in array is as small as nearly one, photons are detected by the plurality of SSPDs or Geiger mode APDs in one light detector, so that a light intensity incidence range in which fluorescence from the specimen S is detectable can be widened. Accordingly, the saturation level of luminance when imaging is performed can be improved.

Figure 4:
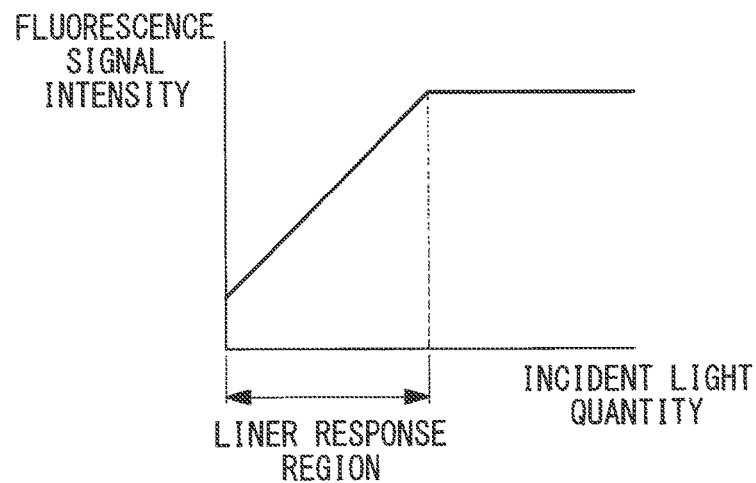
FIG. 4 is a graph showing the relationship between the incident light quantity of a light detector and the intensity of a detection signal in the laser microscope system in FIG. 1.

In the present embodiment, the signal adder 37 may include a storage unit that stores the lower limit value and the upper limit value of a linear response region, where the intensity of a signal linearly changes with respect to the incident light quantity of each of the light detectors 29A, 29B, and 29C, as shown in FIG. 4, for example, such that, in accordance with the lower limit value and the upper limit values of the linear response region with respect to each of the light detectors 29A, 29B, and 29C stored in the storage unit, only values within the linear response region are extracted from the detection signals and added together.

Accordingly, an image signal having a wide linearity can be generated.

Figure 5:
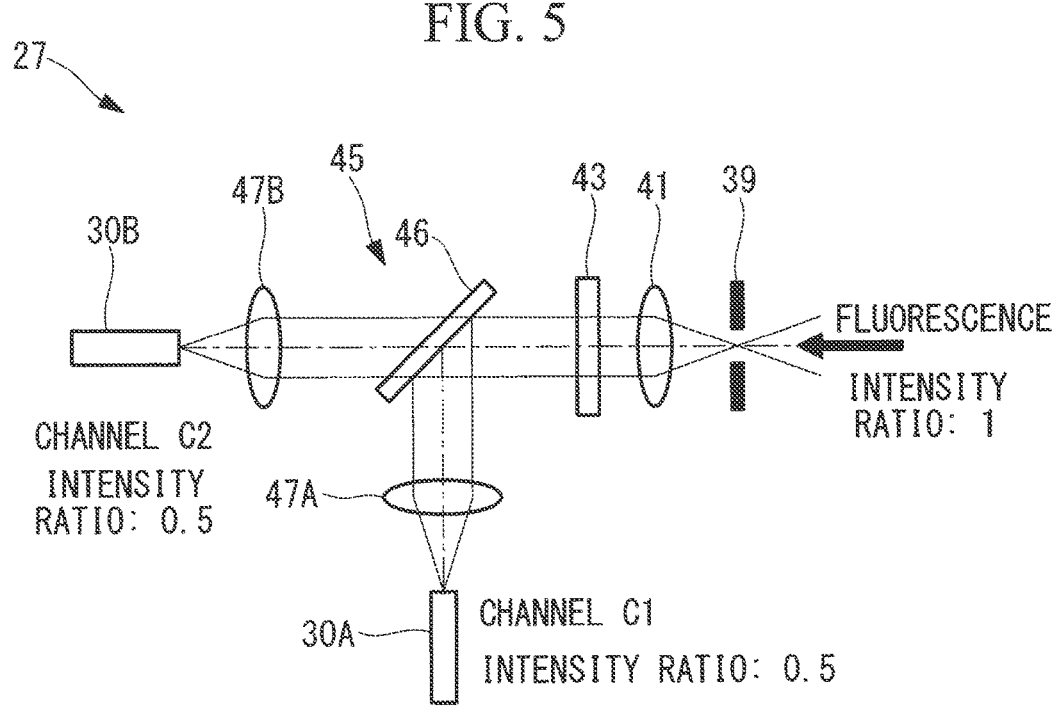
FIG. 5 is a schematic diagram illustrating another example of a light path branching unit in the laser microscope system according to the first embodiment of the present invention.

In the present embodiment, the example in which the single detection light path is branched to the three channels C1, C2, and C3 with use of the two partial reflection mirrors 46A and 46B has been described. However, the single detection light path may be branched to two or more arbitrarily defined channels. The light path branching unit 45 may include one partial reflection mirror 46 such that the single detection light path is branched to the two channels C1 and C2, as illustrated in FIG. 5, for example. In this case, the branch ratio may be changed with the reflectance of the partial reflection mirror 46. In the example illustrated in FIG. 5, fluorescence having a strength ratio of 1 is branched to fluorescence having a strength ratio of 0.5 and fluorescence having a strength ratio of 0.5.

The present embodiment can be modified as follows.

In a first modification, the light path branching unit 45 may include, in place of the partial reflection mirror 46, a polarization beam splitter (polarization element) 51 that branches fluorescence according to the polarization component, as illustrated in FIG. 6, for example.

Accordingly, unpolarized fluorescence (unpolarized light) can be branched into the channel C1 of S-polarized fluorescence (S-polarized light) and the channel C2 of P-polarized fluorescence (P-polarized light) at the substantially equal ratio. Also in this case, an effect similar to that of the present embodiment can be provided.

In a second modification, the light path branching unit 45 may include, in place of the partial reflection mirror 46, a light dividing element 53 such as a linear variable filter that branches fluorescence in a single detection light path according to the wavelength, as illustrated in FIG. 7, for example.

Accordingly, fluorescence in a single detection light path can be branched into the plurality of channels C1 and C2 at the branch ratio corresponding to wavelength characteristics of the light dividing element 53.

A linear variable filter reflects fluorescence of different wavelengths according to the incidence position of the fluorescence. Therefore, the light dividing element 53 may be moved according to the wavelength of fluorescence to be detected and reflect the fluorescence such that the wavelength to be branched is changed. Also in this case, an effect similar to that of the present embodiment can be provided.

In a third modification, without the optical fiber 31 being provided, the light path branching unit 45 may include, in place of the partial reflection mirror 46, a fiber coupler (star coupler) 55 having one entrance end and a plurality of branched exit ends, as illustrated in FIG. 8, for example. In FIG. 8, reference numeral 47 denotes a collecting lens.

The fiber coupler 55 is formed by heating, melting, fusing, and drawing a plurality of optical fibers, and has one entrance end 54 and two exit ends 56A and 56B.

According to the present modification, the branch ratio of fluorescence can be adjusted by the characteristics of the fiber coupler 55. Also, the branch ratio of fluorescence may be adjusted by attachment of a light attenuator to the optical fibers forming the fiber coupler 55. Moreover, the flexibility in installation can be further improved, with a simple configuration, by the characteristics of the optical fibers forming the fiber coupler 55, compared to a case where the light path is branched by a mirror or the like.

Figure 9:
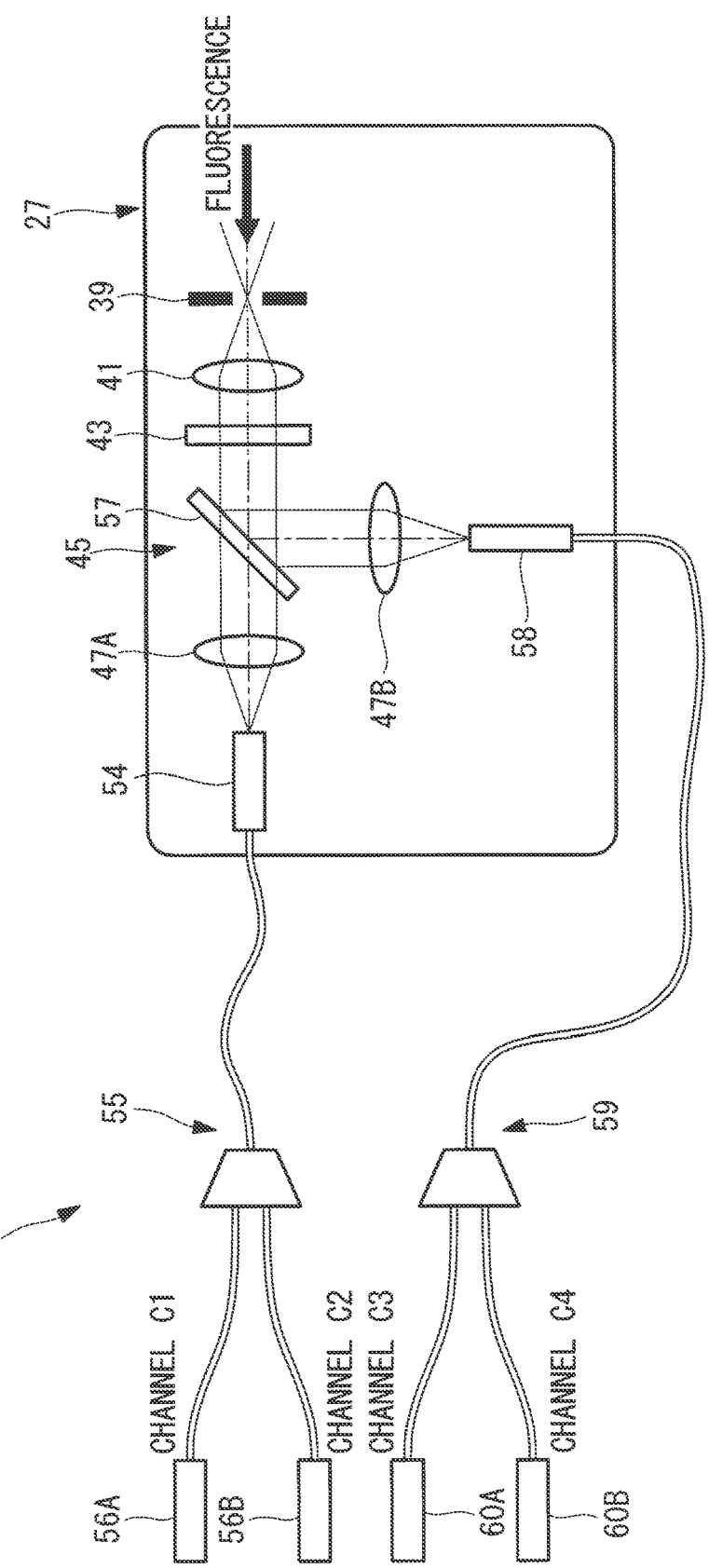
FIG. 9 is a schematic diagram illustrating another example of the light path branching unit in the laser microscope system according to the third modification of the first embodiment of the present invention.

In the present modification, the light path branching unit 45 may use a dichromic mirror 57 that branches, on a wavelength basis, fluorescence in a single detection light path from the multi-dyed specimen S into two light paths, and two fiber couplers 55 and 59 that further branch, into two light paths, the fluorescence having been branched, on a wavelength basis, into the two light paths by the dichromic mirror 57, as illustrated in FIG. 9, for example.

Accordingly, with a simple configuration, fluorescence in a single detection light path can be branched into the four channels C1, C2, C3, and C4, and the branch ratio thereof can also be adjusted by the characteristics of the fiber couplers 55 and 59, etc. In FIG. 9, reference numeral 58 denotes an entrance end of the fiber coupler 59 and reference characters 60A and 60B denote exit ends of the fiber coupler 59.

Figure 10:
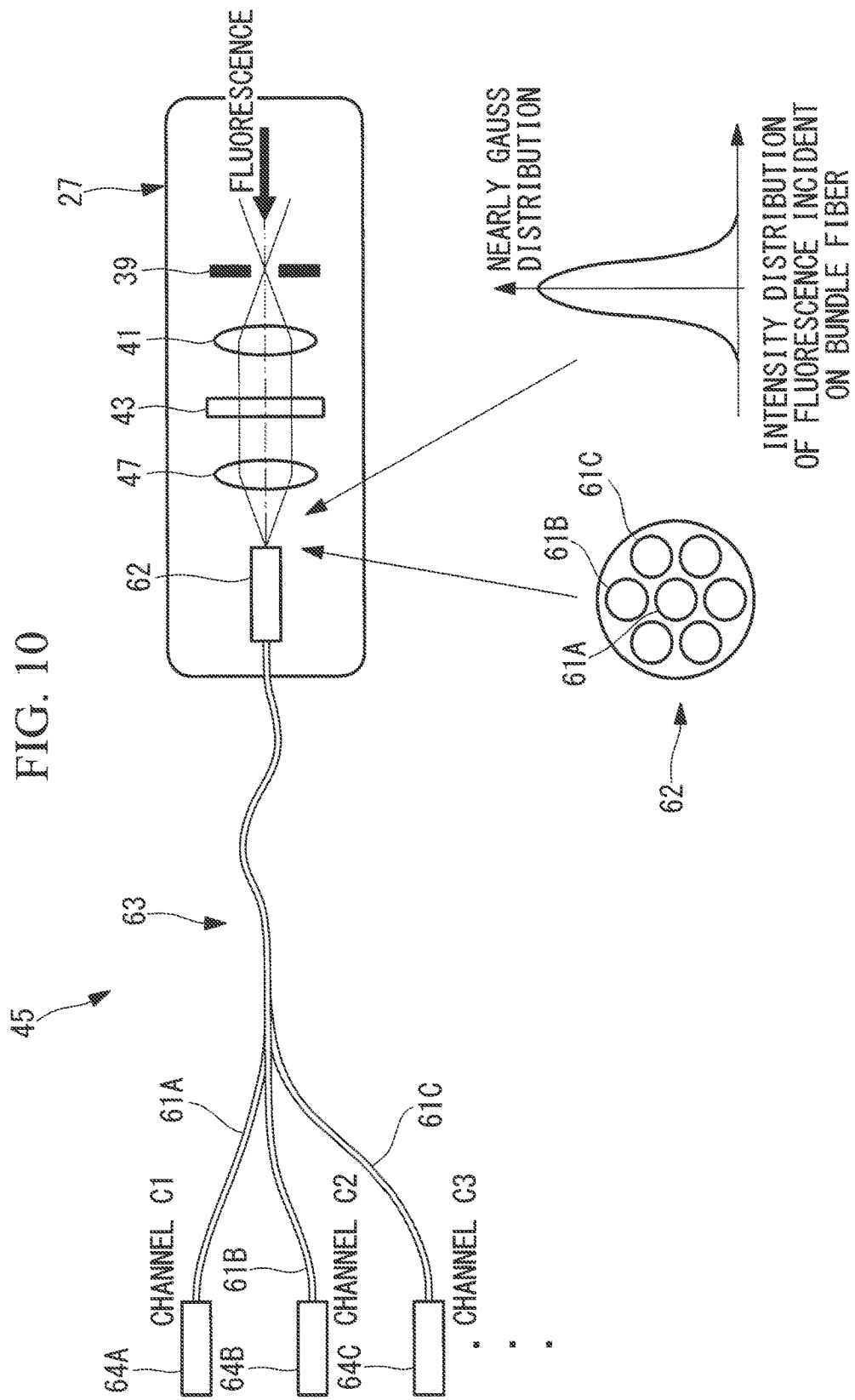
FIG. 10 is a schematic diagram illustrating one example of a light path branching unit in a laser microscope system according to a fourth modification of the first embodiment of the present invention.

In a fourth modification, the light path branching unit 45 may include, in place of the partial reflection mirror 46, a bundle fiber 63 formed of a plurality of optical fibers 61A, 61B, and 61C bundled together, as illustrated in FIG. 10, for example. In FIG. 10, reference numeral 62 denotes an entrance end of the bundle fiber 63, and reference characters 64A, 64B, and 64C denote a plurality of exit ends of the bundle fiber 63.

Accordingly, fluorescence in a single detection light path can be branched in space into the channels C1, C2, and C3 by the bundle fiber 63. The present modification is described by showing the optical fibers 61A, 61B, and 61C among the plurality of optical fibers forming the bundle fiber 63 and the light detectors 29A, 29B, and 29C among the plurality of light detectors.

In the present modification, for example, the plurality of optical fibers 61A, 61B, and 61C forming the bundle fiber 63 may be associated with the light detectors 29A, 29B, and 29C, respectively, such that fluorescence in a single detection light path is branched into the plurality of channels C1, C2, and C3 the number of which is equal to the number of the optical fibers 61A, 61B, and 61C.

In the present modification, the signal adder 37 may have a function as a signal selecting unit that selects, in accordance with the relationship between the light quantity of fluorescence incident on the bundle fiber 63 and arrangement of the optical fibers 61A, 61B, and 61C in the bundle fiber 63, detection signals to be added together.

In this case, for example, for fluorescence the light quantity of which is so high as to be equal to or higher than a prescribed threshold, all the detection signals of the channels C1, C2, and C3 from the light detectors 29A, 29B, and 29C may be added together, and a single image signal may be generated, whereas for incident fluorescence the light quantity of which is so low as to be lower than the prescribed threshold, only the detection signal from the one light detector 29A, to which the optical fiber 61A disposed at the center in the radial direction of the bundle fiber 63 is allocated, may be selected, and a single image signal may be generated.

As shown in FIG. 10, when the light quantity of fluorescence incident on the bundle fiber 63 is low, the intensity peak of the incident fluorescence is at the center portion of the light flux, and very little fluorescence may be incident on the optical fibers 61B and 61C, etc. which are disposed in the radially circumferential portion of the bundle fiber 63. In this case, detection signals from the light detector 29B and 29C, etc., to which the optical fibers 61B and 61C, etc. in the circumferential portion are allocated, are unnecessary in the adding. Therefore, only a detection signal from the light detector 29A, to which the optical fiber 61A at the center is allocated, is used, and thus, the number of detection signals to be added together is reduced. Accordingly, addition of noise from the light detectors 29B and 29C due to such adding can be eliminated.

In the present modification, the optical fiber 61A disposed at the radial center portion of the bundle fiber 63 may be allocated to the light detector 29A, and a plurality of the optical fibers 61B and 61C disposed in the circumferential portion of the bundle fiber 63 may be bundled together and allocated to the other light detector 29B.

In the present modification, for example, when the light quantity of incident fluorescence is low, the fluorescence may be detected by the light detector 29A only, to which the optical fiber 61A disposed at the radial center of the bundle fiber 63 is allocated, and the total quantity of the fluorescence may be calculated from the light quantity detected by the light detector 29A and the detection efficiency of all the light detectors 29A, 29B, and 29C. On the other hand, when the light quantity of incident fluorescence is high, fluorescence may be detected by the light detectors 29B and 29C only, to which the plurality of optical fibers 61B and 61C disposed in the radially circumferential portion of the bundle fiber 63 are allocated, and the total quantity of the fluorescence may be calculated from the light quantities detected by the plurality of light detectors 29B and 29C and the detection efficiency of all the light detectors 29A, 29B, and 29C.

Accordingly, the signal intensity of a detection signal can be increased and an image signal having a higher S/N ratio can be generated.

Figure 11:
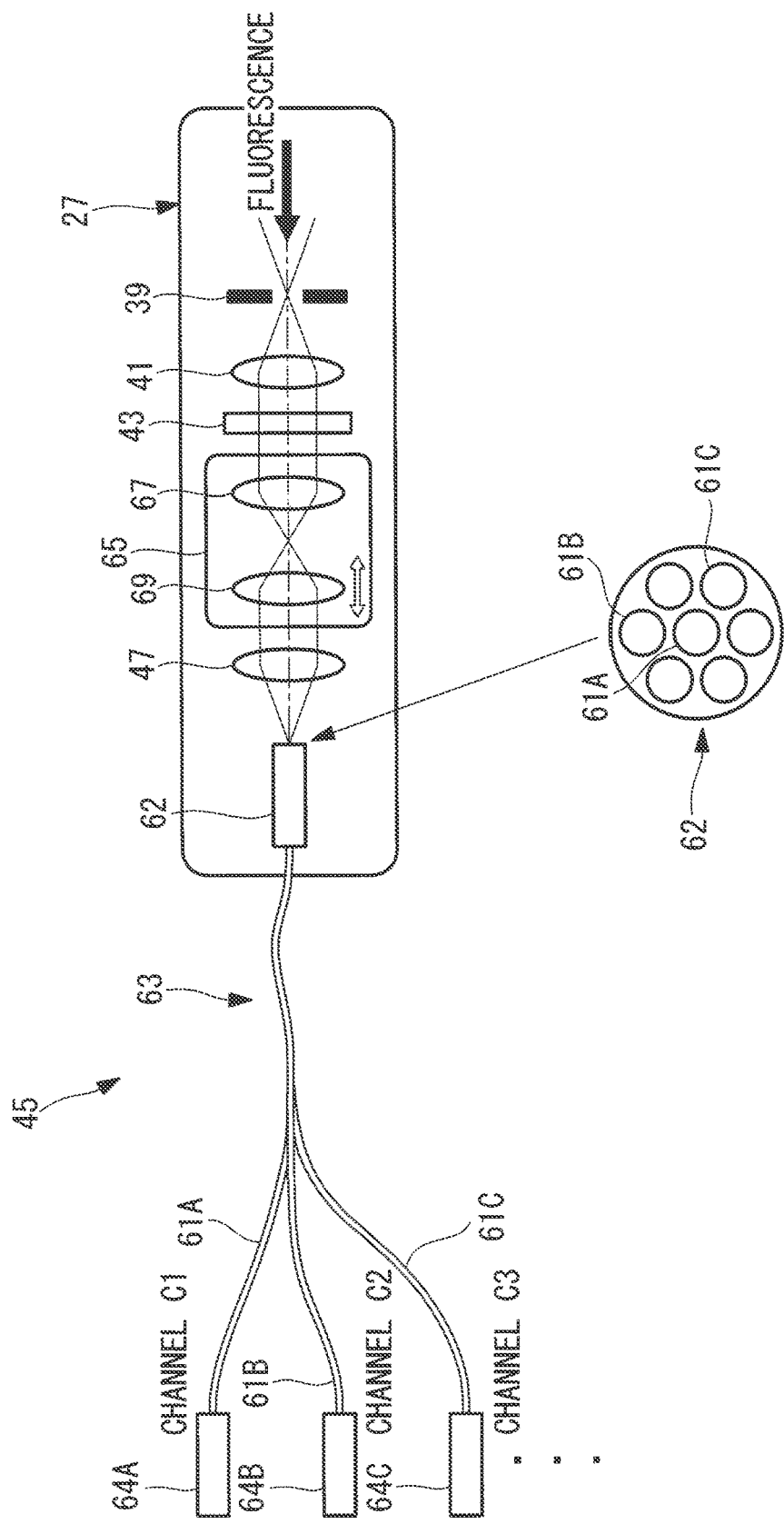
FIG. 11 is a schematic diagram illustrating another example of the light path branching unit in the laser microscope system according to the fourth modification of the first embodiment of the present invention.

In the present modification, the light path branching unit 45 may further include a light flux diameter changing unit 65 that changes the light flux diameter of fluorescence incident on the bundle fiber 63, as illustrated in FIG. 11, for example. For example, the light flux diameter changing unit 65 may be formed of a fixed lens 67 disposed at the front side between the bandpass filter 43 and the collecting lens 47, a movable lens 69 disposed on the rearward side thereof, and a moving mechanism (not illustrated) that moves the movable lens 69 in a direction along the optical axis, and may change the light flux diameter of the fluorescence through movement of the movable lens 69 caused by the moving mechanism.

In this case, for example, when the light quantity of incident fluorescence is high, the light flux diameter changing unit 65 may increase the light flux diameter of the fluorescence incident on the bundle fiber 63, so as to widen the fluorescence to the radial circumferential portion of the bundle fiber 63. Accordingly, fluorescence is incident on all the optical fibers 61A, 61B, and 61C forming the bundle fiber 63, so that the number of branches of light can be increased and the image saturation level can be improved.

On the other hand, when the light quantity of incident fluorescence is low, the light flux diameter changing unit 65 may reduce the light flux diameter of the fluorescence incident on the bundle fiber 63, so as to collect the fluorescence on the radial center portion of the bundle fiber 63. Accordingly, fluorescence may be incident on only the optical fiber 61A disposed at the radial center of the bundle fiber 63 such that the unnecessary optical fibers 61B and 61C in the circumferential portion are not used. Thus, addition of noise from the light detectors 29B and 29C can be eliminated.

For example, an adjustment procedure of the light flux diameter of fluorescence to be performed by the light flux diameter changing unit 65, may include: adjusting the position of the movable lens 69 such that the light detectors 29A, 29B, and 29C for the channels C1, C2, and C3 do not reach saturation levels and the total value of all the detection signals of the channels C1, C2, and C3 from the light detectors 29A, 29B, and 29C becomes the largest; and subsequently, while shifting the position of the movable lens 69 to such a degree not to reduce the total values of the detection signals, blocking incidence of fluorescence in order from the optical fibers 61B and 61C disposed in the radial circumferential portion of the bundle fiber 63.

Accordingly, an image signal having a higher S/N ratio can be generated.

Second Embodiment

Next, a light detecting device and a laser microscope system according to a second embodiment of the present invention is described.

The light detecting device 5 and the laser microscope system 1 according to the present embodiment differ from those of the first embodiment in that the signal adder 37 of the present embodiment uses the branch ratios of fluorescence of respective channels as coefficients of the detection signals.

Hereinafter, components the same as those in the light detecting device 5 and the laser microscope system 1 according to the first embodiment are denoted by the same reference characters and explanations thereof are omitted.

Similarly to the light detecting device 5 illustrated in FIG. 5, for example, the light detecting device 5 according to the present embodiment may use, as a light path branching unit, the light path branching unit 45 including the one partial reflection mirror 46. In the present embodiment, the partial reflection mirror 46 is configured to have reflection characteristics to reflect the fluorescence in a single detection light path to the channel C1 at the branch ratio of 0.9 and to the channel C2 at the branch ratio of 0.1.

The signal adder 37 according to the present embodiment includes a storage unit (not illustrated) that stores the branch ratio of fluorescence for each channel, and multiplies the branch ratios to corresponding detection signal stored in the storage unit, as shown in the following equation (2) and adds the resultant detection signals together, and thereby, generates an image signal.

Image signal=(1/branch ratio 0.9 of channel $C1$)× detection signal of channel $C1$ from light detector $29A$+(1/branch ratio 0.1 of channel $C2$)× detection signal of channel $C2$ from light detector $29B$ (2)

With the light detecting device 5 and the laser microscope system 1 according to the present embodiment, while the S/N ratio is ensured, an image signal having a higher saturation level can be generated, compared to a case where two or more detection signals are simply added together. The present embodiment is effective for a case where a bright region such as the region of the specimen S and a dark region such as a background coexist.

In the present embodiment, for example, for fluorescence the light quantity of which is within a range of a predetermined threshold, the signal adder 37 may multiply detection signals with the branch ratios and adds the resultant detection signals together. However, when fluorescence having a luminance lower than the predetermined threshold is incident, an image signal may be generated by use of only a detection signal of the channel C1, the branch ratio for which is high, outputted from the light detector 29A, and when fluorescence having a luminance higher than the predetermined threshold is incident, an image signal may be generated by use of only a detection signal of the channel C2, the branch ratio for which is low, outputted from the light detector 29B. Accordingly, an image signal having a high saturation level can be generated when low luminance fluorescence is incident, and an image signal having a high S/N ratio can be generated when high luminance fluorescence is incident.

The present embodiment can be modified as follows.

In a first modification, for example, the signal adder 37 may use, as coefficients, the sensitivities of the light detectors 29A and 29B and/or the amplifier gains of the detection circuits 33A and 33B, in addition to the branch ratios.

Due to difference of the respective detection efficiencies between the light detectors 29A and 29B, an effect similar to an effect of the branch ratios can be obtained from the sensitivities of the light detectors 29A and 29B. The amplifier gains of the detection circuits 33A and 33B may be set to correspond to the sensitivities of the light detectors 29A and 29B and the branch ratios, so that the levels of the respective detection signals of the channels C1 and C2 can be made equal to each other, whereby design commonization of a mechanism for forming an image based on the detection signals of the channels C1 and C2 is facilitated. The sensitivities of the light detectors 29A and 29B may be obtained from the sensitive characteristics of the light detectors 29A and 29B, or may be obtained from values of current from a current supplying unit which supplies bias current to the light detectors 29A and 29B.

In this case, the signal adder 37 may multiply detection signals with the branch ratios, the sensitivities of the light detectors 29A and 29B, and the amplifier gains of the detection circuits 33A and 33B as coefficients, and add the resultant detection signals together so as to generate a single image signal, as shown in the following equation (3).

Image signal={1/(branch ratio of channel C1×detection efficiency of light detector 29A with respect to channel C1×amplifier gain of detection circuits 33A with respect to channel C1}×detection signal of channel C1 from light detector 29A+ {1/(branch ratio of channel C2×detection efficiency of light detector 29B with respect to channel C2×amplifier gain of detection circuit 33B with respect to channel C2}×detection signal of channel C2 from light detector 29B  (3)

Accordingly, an image signal having a higher saturation level can be generated due to the differences between the sensitivities of the light detectors 29A and 29B and the amplifier gains of the detection circuits 33A and 33B, compared to a case where detection signals are multiplied with only the branch ratio. When the amplifier gains of the detection circuits 33A and 33B are not used as coefficients, the amplifier gains of the detection circuits 33A and 33B with respect to the channels C1 and C2 may be removed from the above equation (3).

In the present modification, light detectors of the same type may be used as the plurality of light detectors 29A and 29B. Accordingly, noise performance can be made equivalent between all the channels C1 and C2. For example, when both the light detectors 29A and 29B are SSPDs having low noise, an image signal obtained by adding can also be made to have low noise.

As the plurality of light detectors 29A and 29B, light detectors of different types may be used. A detector with high sensitivity such as an SSPD may be used for the channel C1 for which the branch ratio is high and a detector with low sensitivity such as a PMT may be used for the channel C2 for which the branch ratio is low. In this case, an image signal having wider information about a weak light region to a high intensity region can be generated. Since there are a variety of types, other than PMTs, of the detector with low sensitivity, improvement of a saturation level can be easily achieved.

In a second modification, when the luminance of a detection signal from the light detector 29A is higher than a luminance saturation value, the signal adder 37 may estimate a luminance value higher than the luminance saturation value on the basis of a detection signal from the other light detector 29B, and substitute the estimated luminance value for the luminance saturation value in the adding.

In this case, a true detection signal of a saturation luminance pixel in the channel C1 may be calculated from the following relational expression (4).

True detection signal of saturation luminance pixel in channel C1=(branch ratio of channel C1×detection efficiency of light detector 29A with respect to channel C1×amplifier gain of detection circuit 33A with respect to channel C1)× detection signal of channel C2/(branch ratio of channel C2×detection efficiency of light detector 29B with respect to channel C2×amplifier gain of detection circuit 33B with respect to channel C2)  (4)

Accordingly, an image signal having clear information about a weak light region can be generated. Also in the present modification, when the amplifier gains of the detection circuits 33A and 33B are not used as coefficients, the amplifier gains of the detection circuits 33A and 33B with respect to the channels C1 and C2 may be removed from the above expression (4).

Third Embodiment

Next, a light detecting device and a laser microscope system according to a third embodiment of the present invention are described.

Figure 12:
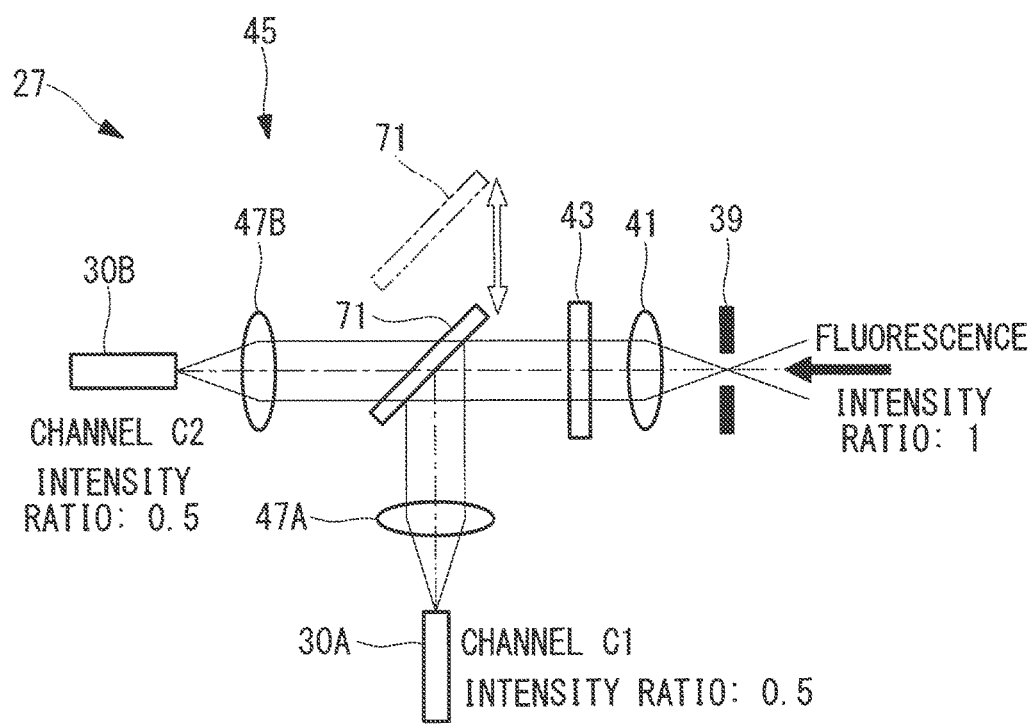
FIG. 12 is a schematic diagram illustrating the light path branching optical system in the laser microscope system according to the first embodiment of the present invention.

The light detecting device 5 and the laser microscope system 1 according to the present embodiment differ from those of the first embodiment in that the light path branching unit 45 of the present embodiment includes, in place of the partial reflection mirror 46, a total reflection mirror (reflection mirror) 71 that reflects fluorescence, and an insertion/removal mechanism (not illustrated) that inserts and removes the total reflection mirror 71 into and from a detection light path, as illustrated in FIG. 12, for example.

Hereinafter, components the same as those of the light detecting device 5 and the laser microscope system 1 according to the first embodiment are denoted by the same reference characters, and explanations thereof are omitted.

In the present embodiment, the light path branching unit 45 reflects fluorescence to the channel C1 upon insertion of the total reflection mirror 71 into the detection light path by the insertion/removal mechanism, and causes the fluorescence to be transmitted to the channel C2 upon removal of the total reflection mirror 71 from the detection light path. Accordingly, fluorescence of a single detection light path can be branched in time into the plurality of channels C1 and C2.

In the present embodiment, light detectors having different detection sensitivities are used as the light detectors 29A and 29B for the channels C1 and C2. For example, if the detection signal is not saturated when the light detector 29A having a high detection sensitivity for the channel C1 detects fluorescence, the light detector 29A for the channel C1 may be used, whereas if the detection signal is saturated when the light detector 29A for the channel C1 detects fluorescence, the light detector 29B having a low detection sensitivity for the channel C2 may be used.

For example, in a case where an SSPD is used as the light detector 29A and a PMT is used as the light detector 29B, an image the weak light region of which has high definition but in which halation occurs due to the low saturation level is acquired by the light detector 29A formed of an SSPD, and an image the high intensity region of which has high definition but the weak light region of which is undetectable due to the low detection sensitivities is acquired by the light detector 29B formed of a PMT.

In this case, at the same wavelength region and under the same condition, fluorescence is detected while the light detector 29A formed of an SSPD and the light detector 29B formed of a PMT are switched by the light path branching unit 45, and the detection signals are added together by the signal adder 37, so that an image signal having a wide linearity can be generated.

The embodiments of the present invention have been described above in detail with reference to the drawings. However, the specific configuration of the present invention is not limited to these embodiments, and encompasses a design modification, etc. within a range of the scope of the present invention. For example, without being limited to the aforementioned embodiments, the present invention may be applied to an embodiment obtained by combining these embodiments, as appropriate. The present invention is not limited to a particular embodiment.

As a result, the following aspects can be introduced by the aforementioned embodiments.

A first aspect of the present invention is a light detecting device including: a light path branching unit that branches a single detection light path of observation light from a specimen, into a plurality of branched light paths; a plurality of light detectors that are provided to the respective branched light paths branched by the light path branching unit and that include an SSPD or a Geiger mode APD to detect the observation light; and a signal generating unit that generates a single image signal in accordance with detection signals outputted from the plurality of light detectors.

According to the present aspect, the light branching unit branches the single detection light path of the observation light generated at the specimen, into the plurality of branched light paths, and the observation light in each of the branched light paths is detected by any of the plurality of light detectors including an SSPD or a Geiger mode APD. Accordingly, it is possible to, while avoiding saturation by suppressing the incident light quantity of each of the light detectors, increase the number of photons countable per unit time by the number of the light detectors, and thereby, improve the maximum counting rate of photons.

In this case, the single image signal may be generated by the signal generating unit in accordance with the detection signals obtained from the light detectors, so that the saturation level of luminance when imaging is performed is further improved, compared to a case where a single light detector is used or a case where one photon is detected by a multi-pixel light receiving element.

In the aforementioned aspect, at least one of the light detectors may be formed by an array of a plurality of the SSPDs or the Geiger mode APDs.

With this configuration, even if the number of photons that are detectable per unit time by each SSPD or Geiger mode APD is as small as nearly one, photons are detected by the plurality of SSPDs or Geiger mode APDs in one light detector, so that a light intensity incidence range in which observation light from the specimen is detectable can be widened. Accordingly, the saturation level of luminance when imaging is performed can be improved.

In the aforementioned aspect, the light path branching unit may include a partial reflection mirror that allows a part of the observation light to transmit therethrough and reflects the rest of the observation light.

With this configuration, observation light in a single detection light path can be branched into a plurality of branched light paths at the intensity ratio corresponding to the transmittance and reflection characteristics of the partial reflection mirror.

In the aforementioned aspect, the light path branching unit may include a polarization element that branches the observation light according to a polarization component.

With this configuration, an effect the same as that provided when a partial reflection mirror is used as the light path branching unit, can be obtained.

In the aforementioned aspect, the light path branching unit may include a light dividing element that branches the observation light according to a wavelength.

With this configuration, observation light in a single detection light path can be branched into a plurality of branched light paths at the branch ratio corresponding to the wavelength characteristics of the light dividing element.

In the aforementioned aspect, the light path branching unit may include a fiber coupler having one entrance end and a plurality of branched exit ends.

With this configuration, the branch ratio of observation light can be adjusted according to the characteristics of the fiber coupler, and further, the branch ratio of observation light can be adjusted even by a fiber-based light attenuator. In addition, the characteristics of the fiber coupler can further improve installation flexibility with a simple configuration, compared to a case where a light path is branched by a mirror or the like.

In the aforementioned aspect, the light path branching unit may include a bundle fiber formed of a plurality of optical fibers bundled together.

With this configuration, observation light in a single detection light path can be branched in space into a plurality of branched light paths by the bundle fiber.

In the aforementioned aspect, the light detecting device may include a signal selecting unit that selects, in accordance with the relationship between the light quantity of the observation light incident on the bundle fiber and arrangement of the optical fibers in the bundle fiber, the detection signal from which the image signal is generated by the signal generating unit.

The observation light incident on the bundle fiber has an intensity distribution in which the intensity becomes higher toward the radial center portion of the light flux and becomes lower away from the radial center of the light flux. Thus, when the incident light quantity of the observation light is reduced, the light quantities detected by the light detectors to which optical fibers disposed to be separate from the radial center of the bundle fiber are allocated, are also reduced. Detection signals outputted from these light detectors may be unnecessary for generation of an image signal. Accordingly, the signal selecting unit selects a detection signal for use in generation of an image signal according to the light quantity of the observation light, so that the S/N ratio of an image signal can be further improved.

In the aforementioned aspect, a light flux diameter changing unit that changes the light flux diameter of observation light incident on the bundle fiber, may be provided.

With this configuration, the light flux diameter changing unit changes the light flux diameter of observation light so that the branch ratios of observation light to be incident on the light detectors can be changed. Accordingly, flexibility of setting of the branch ratios can be improved.

In the aforementioned aspect, the signal generating unit may generate the image signal by adding two or more of the detection signals together.

With this configuration, the respective detection signals from the plurality of light detectors are added together so that the image signal accordingly having a high S/N ratio can be generated.

In the aforementioned aspect, a storage unit that stores the branch ratios of the observation light for the respective branched light paths may be provided, and the signal generating unit may multiply the detection signals with the corresponding branch ratios stored in the storage unit, and add the resultant detection signals together.

With this configuration, the image signal having a higher saturation level while the S/N ratio thereof is ensured, can be generated, compared to a case where two or more detection signals are simply added together. This is effective for a case where a bright region such as the region of a specimen and a dark region such as a background coexist, such as a case where a cell specimen is observed.

In the aforementioned aspect, a storage unit that stores the lower limit value and the upper limit value of a linear response region in which the intensity of a signal from each of the light detectors linearly changes with respect to the incident light quantity may be provided, and, in accordance with the lower limit value and the upper limit value of the linear response region of each of the light detectors stored in the storage unit, the signal generating unit may extract only values within the linear response regions from the detection signals and add the values together.

With this configuration, an image signal having wide linearity can be generated.

In the aforementioned aspect, when the luminance of the detection signal from any one of the light detectors is higher than a luminance saturation value, the signal generating unit may estimate a luminance value higher than the luminance saturation value in accordance with the detection signals from the other light detectors and substitute the estimated luminance value for the luminance saturation value in the adding.

With this configuration, the image signal having clear information about the weak light region thereof can be generated.

In the aforementioned aspect, the light path branching unit may include a reflection mirror that reflects the observation light, and an insertion/removal mechanism that inserts and removes the reflection mirror to and from the detection light path.

With this configuration, observation light in a single detection light path can be branched in time into a plurality of branched light paths by switching of insertion and removal of the reflection mirror into and from the reflection mirror by the insertion/removal mechanism.

A second aspect of the present invention is a laser microscope system including: a light scanning unit that scans the specimen with laser light emitted from a laser light source; any one of the light detecting devices which detects the observation light returning from the specimen after the scanning with the laser light by the light scanning unit; and a cryocooler that cools the light detector formed of the SSPD or Geiger mode APD in the light detecting device.

According to the present aspect, when laser light emitted from the laser light source scans the specimen by an operation of the light scanning unit, observation light returning from scanning positions of the specimen is detected by the plurality of light detectors of the light detecting device. In this case, the light detectors formed of SSPDs or Geiger mode APDs are held in a cooled state by the cryocooler, so that the observation light can be detected with high quantum efficiency and low and dark noise.

According to the present invention, an effect of enabling improvement of a luminance saturation level when imaging is performed, is provided.

REFERENCE SIGNS LIST 1 laser microscope system
5 light detecting device
7 cryocooler
29, 29A, 29B, 29C light detector
37 signal adder (signal generating unit)
45 light path branching unit
46, 46A, 46B partial reflection mirror
51 polarization beam splitter (polarization element)
53 light dividing element
55 fiber coupler
63 bundle fiber
65 light flux diameter changing unit
71 total reflection mirror (reflection mirror)
S specimen

The invention claimed is:

1. A light detecting device comprising:
a light path branching unit that branches a single detection light path of observation light from a specimen, into a plurality of branched light paths;
a plurality of light detectors that are provided to the respective branched light paths branched by the light path branching unit and that include an SSPD or Geiger mode APD to detect the observation light; and
a signal generating unit that generates a single image signal in accordance with detection signals outputted from the plurality of light detectors.

2. The light detecting device according to claim 1, wherein at least one of the light detectors is formed by an array of a plurality of the SSPDs or a plurality of the Geiger mode APDs.

3. The light detecting device according to claim 1, wherein the light path branching unit includes a partial reflection mirror that allows a part of the observation light to pass therethrough and reflects the rest of the observation light.

4. The light detecting device according to claim 1, wherein the light path branching unit includes a polarization element that branches the observation light according to a polarization component.

5. The light detecting device according to claim 1, wherein the light path branching unit includes a light dividing element that branches the observation light according to a wavelength.

6. The light detecting device according to claim 1, wherein the light path branching unit includes a fiber coupler having one entrance end and a plurality of branched exit ends.

7. The light detecting device according to claim 1, wherein the light path branching unit includes a bundle fiber formed of a plurality of optical fibers bundled together.

8. The light detecting device according to claim 7, further comprising
a signal selecting unit that selects, in accordance with a relationship between a light quantity of the observation light incident on the bundle fiber and arrangement of the optical fibers in the bundle fiber, the detection signal from which the image signal is generated by the signal generating unit.

9. The light detecting device according to claim 7, further comprising
a light flux diameter changing unit that changes a light flux diameter of the observation light incident on the bundle fiber.

10. The light detecting device according to claim 1, wherein the signal generating unit generates the image signal by adding two or more of the detection signals together.

11. The light detecting device according to claim 10, further comprising
a storage unit that stores branch ratios of the observation light for the respective branched light paths, wherein
the signal generating unit multiples the branch ratios stored in the storage unit with the corresponding detection signals, and adds the resultant detection signals together.

12. The light detecting device according to claim 10, further comprising
a storage unit that stores a lower limit value and an upper limit value of a linear response region in which an intensity of a signal from each of the light detectors linearly changes with respect to the incident light quantity, wherein
in accordance with the lower limit value and the upper limit value of the linear response region of each of the light detectors stored in the storage unit, the signal generating unit extracts only values in the linear response region from the detection signals and adds the values together.

13. The light detecting device according to claim 10, wherein when a luminance of the detection signal from any one of the light detectors is higher than a luminance saturation value, the signal generating unit estimates a luminance value higher than the luminance saturation value in accordance with the detection signals from the other light detectors, and substitutes the estimated luminance value for the luminance saturation value in the adding.

14. The light detecting device according to claim 1, wherein the light path branching unit includes a reflection mirror that reflects the observation light, and an insertion/removal mechanism that inserts and removes the reflection mirror into and from the detection light path.

15. A laser microscope system comprising:
a light scanning unit that scans the specimen with laser light emitted from a laser light source;
the light detecting device according to claim 1 which detects the observation light returning from the specimen after the scanning with the laser light by the light scanning unit; and
a cryocooler that cools the light detector formed of the SSPD or the Geiger mode APD in the light detecting device.

* * * * *